United States Patent [19]

Wiley

[11] 4,083,706
[45] Apr. 11, 1978

[54] STERILE TRAP ACCESSORY FOR USE WITH SURGICAL ASPIRATOR

[76] Inventor: Corless W. Wiley, 1505 Junior Dr., Dallas, Tex. 75208

[21] Appl. No.: 656,367

[22] Filed: Feb. 9, 1976

Related U.S. Application Data

[63] Continuation-in-part of Ser. No. 517,935, Oct. 25, 1974, abandoned.

[51] Int. Cl.² .................. B01D 49/00; A61C 17/04; A61M 1/00
[52] U.S. Cl. ..................... 55/385 R; 32/33; 55/374; 55/497; 55/503; 55/504; 55/511; 128/276
[58] Field of Search .............. 128/276, 278, 2 F; 32/33; 55/385 R, 373, 374, 478, 480, 503, 504, DIG. 31, 497, 511

[56] References Cited

U.S. PATENT DOCUMENTS

| | | | |
|---|---|---|---|
| 602,572 | 4/1898 | Browne et al. | 32/33 |
| 1,020,782 | 3/1912 | Tinker | 55/503 |
| 1,094,257 | 4/1914 | Schramm et al. | 128/277 |
| 1,246,522 | 11/1917 | Backstrom | 55/503 X |
| 1,353,587 | 9/1920 | Heck | 32/33 |
| 1,583,023 | 5/1926 | Stoloff | 32/33 |
| 3,084,440 | 4/1963 | Wenof | 32/33 |
| 3,344,523 | 10/1967 | Halsey | 32/33 |
| 3,476,144 | 11/1969 | Krantz | 32/33 X |
| 3,610,242 | 10/1971 | Sheridan et al. | 128/2 F X |
| 3,753,292 | 8/1973 | Hutson | 32/33 |
| 3,803,810 | 4/1974 | Rosenberg | 55/DIG. 31 X |
| 3,847,573 | 11/1974 | Gandrud | 32/33 X |
| 3,863,635 | 2/1975 | Swatman | 128/276 |
| 3,889,657 | 6/1975 | Baumgarten | 128/304 X |
| 3,890,712 | 6/1975 | Lopez | 32/33 |

*Primary Examiner*—Frank W. Lutter
*Assistant Examiner*—Kathleen J. Prunner
*Attorney, Agent, or Firm*—Peter J. Murphy

[57] ABSTRACT

A trap accessory, for selective coupling between a suction conduit and an aspirator includes: an elongated housing having a through passage; an elongated retainer slidably received in the housing passage, and having a through passage; and a filter element retained in the housing passage by said retainer. The housing is provided with a coupling nipple for coupling to a complementary coupling orifice in the suction conduit; and the retainer is provided with a coupling orifice for coupling to a complementary coupling nipple of the aspirator. The suction conduit and suction appliance have complementary coupling members, and are adapted to be coupled directly together in the absence of the trap accessory.

8 Claims, 3 Drawing Figures

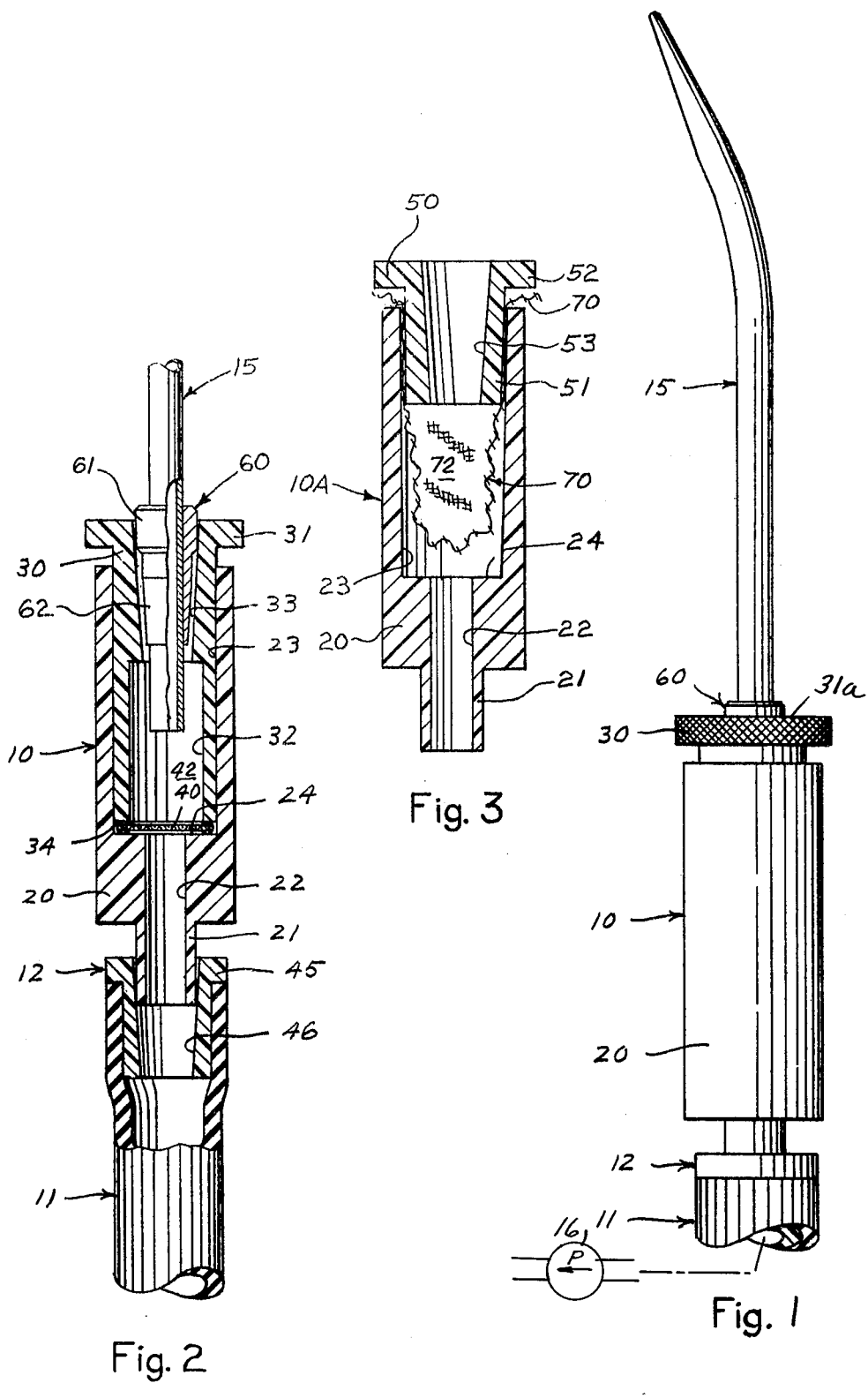

STERILE TRAP ACCESSORY FOR USE WITH SURGICAL ASPIRATOR

REFERENCE TO RELATED APPLICATION

This application is a continuation-in-part of application Ser. No. 517,935, filed Oct. 25, 1974, and now abandoned.

BACKGROUND AND SUMMARY OF THE INVENTION

This invention relates to a trap accessory for use in association with an aspirator, in dental or medical procedures; and to the combination of a trap accessory, aspirator, and suction conduit for use in dental and medical procedures.

In the practice of dentistry or other oral treatment or surgery, it is frequently necessary to remove particles of solid material from the mouth during such treatment; and evacuation systems are used for this purpose. In the use of such system, it is frequently desirable to collect particles removed from the mouth for a number of possible reasons. One important recovery purpose is to enable a surgeon to collect, with relative ease, osseous coagulum, which is osseous material to be grafted into boney peridontal defects. In this case, a sterile trap accessory is essential. Another purpose may be to recover valuable metals which have been used in the filling of teeth for example. Another purpose may be to recover materials from the mouth, from wounds, or from other parts of the body for the purpose of laboratory analysis; and in this case, again, a sterile trap accessory is important.

Another important purpose, of a trap accessory according to the invention, may be to assure that particles which are intended to be removed from a wound or body recess by the suction procedure have, in fact, been removed. One example may be the removal of a root tip of a tooth, which tip has broken off during extraction and remains in the socket. Another example may be to remove fragments of foreign bodies which have been detected in a wound by means of X-ray for example. With the use of this trap, the surgeon can immediately ascertain whether or not the root tip has been removed, or whether or not the known number of foreign body fragments have been removed, by inspecting the contents of the trap. This may minimize or eliminate the necessity for additional x-rays to ascertain whether a particle has in fact been removed.

An important object of this invention is to provide a trap accessory which is adapted to be readily inserted in and removed from an evacuation system, between the distal end of the suction line and an aspirator.

Another object of this invention is to provide a trap accessory which is readily disassembled and reassembled, for the purpose of removing collected material, for the purpose of cleaning the parts of the trap, and for sterilization.

A further object of this invention is to provide a trap accessory which is designed for ease of manufacture, and which is versatile in use.

Still another object of this invention is to provide a trap accessory which is readily cleaned and sterilized, and which is adapted for use in recovering materials from the mouth or body, in a sterile condition for immediate reuse or analysis.

A still further object of this invention is to provide a trap accessory, aspirator, and suction conduit combination, with complementary coupling means for coupling the aspirator to the conduit, either with or without the trap accessory.

These objects are accomplished in a trap for selective use with a surgical aspirator and a flexible suction conduit in a medical or dental evacuation system; wherein that system includes a suction conduit which has means at one end defining a coupling orifice and an aspirator having means at one end defining a coupling nipple, wherein the coupling orifice and coupling nipple are configured for complementary coupling and sealing engagement. The trap includes an elongated housing having means defining a coupling nipple at one end, having a through passage including a smaller bore portion at the one end which passes through the coupling nipple, with the through passage including a cylindrical counterbore opening to the other end. The trap further includes a retainer having a cylindrical body dimensioned to be received in the housing counterbore with a sliding sealing fit and having a radially enlarged gripping means at one end for manipulating the retainer relative to the housing. The retainer also has an axial through passage including a coupling orifice at the one end. The trap further includes a filter element confined between the housing and retainer and defining, with these parts, the collection chamber of the trap. The housing coupling nipple is configured for complementary coupling in sealing engagement with the conduit coupling orifice of the system; and the retainer coupling orifice is configured for complementary coupling and sealing engagement with the aspirator coupling nipple of the system.

Another aspect of the invention is the combination of the trap with the aspirator and with the suction conduit, with the suction conduit coupling orifice being configured for alternative complementary coupling and sealing engagement with either the aspirator coupling nipple or with the trap housing coupling nipple, and with the aspirator coupling nipple being configured for alternative complementary coupling and sealing engagement with either the conduit coupling orifice or with the trap retainer coupling orifice.

The novel features and the advantages of the invention, as well as additional objects thereof will be understood more fully from the following description when read in connection with the accompanying drawing.

DRAWING

FIG. 1 is an elevation view of a trap according to the invention, in assembled relation with a suction conduit and a surgical aspirator;

FIG. 2 is a longitudinal sectional view of the trap and assembled components illustrated in FIG. 1; and FIG. 3 is a longitudinal sectional view of an alternative form of trap.

DESCRIPTION OF THE PREFERRED EMBODIMENTS

In the drawings a trap accessory 10 is shown in assembled relation with a suction conduit 11, provided with a coupling adaptor 12, and with a surgical aspirator 15. These components are a part of a dental or surgical evacuation system which inherently includes some form of suction pump 16 to which the suction conduit 11 is connected.

Referring to FIGS. 1 and 2, one embodiment of a trap accessory is an assembly of a housing component 20, retainer component 30 and a filter component 40.

The housing 20 is preferably fabricated from a relatively rigid plastic material such as tetrafluoroethylene, and is generally cylindrical in shape having a reduced diameter axial extension 21 at one end defining a coupling nipple. The housing is provided with a through passage consisting of a smaller bore portion 22 at the one end extending through the nipple 21, and a counterbore 23 opening to the other end; the counterbore providing a transverse annular shoulder 24 at the juncture with the smaller bore 22. The coupling nipple 21 is preferably cylindrical, having an outer diameter of 7/16 inch for example.

The retainer 30 is also preferably fabricated from a relatively rigid plastic material such as tetrafluoroethylene. The retainer is generally cylindrical in shape, and of a length to be fully received within the housing counterbore 23 and to project from the housing. The retainer body is dimensioned to be received within the housing counterbore with a sliding an sealing fit; and the projecting end is provided with a radial flange 31, preferably having an outer diameter greater than that of the housing, and a knurled or serrated peripheral surface 31a for ease of inserting and removing the plug relative to the housing. The retainer is provided with a through passage consisting of a cylindrical bore 32, extending inward from the inner end of the retainer, and a tapered bore 33, extending inward from the flange end of the retainer and converging from its outer end toward the bore 32. The taper is a slight taper which may have a mid-diameter of about 7/16 inch for example, thereby defining a 7/16 inch taper. The tapered bore 33 functions as a coupling orifice. The inner end of the retainer defines an annular, transverse end face 34 confronting the housing shoulder 24; and the disk-shaped filter component 40 has an outer diameter slightly smaller than that of the housing counterbore 23, and is accordingly confined and retained between the shoulder and plug end face when the plug is fully received in the counterbore. The filter component may be fabricated from a suitable metal screen material confined within a metal rim such as a brass rim, for example. The filter component may include an overlay of a cloth or paper filtering material, for example. In assembled relation, then, the retainer bore 32 with coacting housing shoulder 24 and the filter component 40 define a collection chamber 42.

The suction conduit 11 may be a ½ inch (inner diameter) rubber hose, for example, fitted onto the adaptor 12 preferably fabricated from a suitable plastic material. The adaptor is a sleeve-like member having an external radial flange 45 at one end and having a through tapered bore 46 with a mid-diameter of about 7/16 inch for example. The adaptor bore 46 defines a coupling orifice which corresponds to the retainer coupling orifice 33.

An aspirator 15, illustrated in FIGS. 1 and 2, is a surgical aspirator fabricated from stainless tubing for example, having a ¼ inch inner diameter. This aspirator includes a coupling fitting or adaptor 60 having a larger cylindrical collar portion 61, having a 7/16 inch outer diameter, and having a reduced portion 62 for coupling to hoses or conduits of smaller size than ⅜ inch inner diameter for example. In the assembled relation best illustrated in FIG. 2, the collar portion 61 of the coupling fitting functions as a coupling nipple, and is received in frictional binding coupling relation with the coupling orifice 33 of the retainer 30.

As described heretofore, the outer diameters of the housing coupling nipple 21 and the aspirator coupling nipple 61 are preferably 7/16 inch; and the retainer coupling orifice 33 and the conduit adaptor coupling orifice 46 are provided with a 7/16 inch taper. The conduit coupling orifice then is adapted for ready frictional coupling to either the trap accessory or to the aspirator 15; and the trap coupling orifice is adapted for ready frictional coupling to the aspirator. Since these couplings are friction couplings and sealing couplings, it is obvious that the assembly of the trap to the other components is readily accomplished. By the same token, and because of the same complementary configurations, when it is not necessary or desirable to use the trap 10 the trap is simply removed and the aspirator is readily coupled directly to the hose coupling 12.

While in the above described assemblies, the trap 10 is shown coupled to a ½ inch hose to the adaptor 12, it will be apparent that the trap could be directly assembled to a ⅜ inch hose for example which would be fitted directly over the housing coupling nipple 21. Similarly such hose could be fitted directly over the aspirator coupling nipple 61.

FIG. 3 of the drawing illustrates an alternative form of trap 10A according to the invention, which is a combination of the above described 20, a modified form of retainer 50 and a modified form of filter component 70.

The retainer 50 consists of a shortened cylindrical body 51 having a radially enlarged head 52 to enable gripping of the retainer to insert it and remove it relative to the housing 20. The outer diameter of the body 51 is dimensioned for a free sliding fit within the housing counterbore 23 for a purpose to be described. The enlarged head 52 is preferably larger in diameter than the outer diameter of the housing; and may be knurled at its periphery for easier gripping by the users. The retainer 50 is provided with a tapered through passage 53 which functions as a coupling recess in the same manner as the above described retainer coupling recess 33.

The filter element 70 preferably comprises an elongated generally cylindrical filter sock or bag, which is closed at one end and open at the other end. The bag may be fabricated from a cloth material, of a type known as squeeze cloth for example, or any other suitable material. The term "squeeze cloth" refers to a product named Amalgam Squeeze Cloths, which is a commercially available product marketed by Johnson & Johnson to dentists for the use stated on the package: "to express excess mercury from amalgam filling". As seen in FIG. 3 the length of the filter bag may correspond generally to the depth of the housing counterbore 23. The mouth of the filter bag 70 has a diameter corresponding generally to the diameter of the housing counterbore 23; and the bag is received within the housing counterbore with its open end extending slightly beyond the open end of the housing counterbore; with the retainer body being received within the bag and housing counterbore to firmly clamp the filter bag within the trap. For this purpose, the diameters of the retainer body and housing counterbore are arranged for a much freer fit to accommodate the thickness of the filter bag. In assembled relation, as seen in FIG. 3, the filter bag 70 and coacting housing counterbore 23 and retainer 50 define a collection chamber 72. The closed end of the filter bag is preferably held in spaced relation from the housing shoulder 24 and the opening to the smaller bore 22, this to prevent buildup of collected material in a limited area at the base of the filter corresponding to the diameter of the small bore. This filter element configuration enables easy recovery of the trapped materials from the trap 10A.

The housing 20 and retainers 30 and 50 are preferably fabricated from tetrafluoroethylene (Teflon), since this material will readily withstand required sterilization temperatures, where use as a sterile trap is desired. Another reason for the selection of this material is that the material is easily machinable; and the housing and retainer parts may be readily machined from material of the desired size acquired as bars or rods, which are then cut into the desired lengths and completed with the desired machining operations. It will be apparent that the housing and retainers could be fabricated from other suitable material including synthetic materials and metals.

What has been described is a versatile trap accessory, for use in evacuation systems; the trap being designed for ease of manufacture and convenience of use; for convenience of disassembly and cleaning, and for readily coupling to the suction conduit and aspirator, with the insertion or removal of the trap being accomplished in seconds.

While preferred embodiments of the invention have been illustrated and described, it will be understood by those skilled in the art that changes and modifications may be resorted to without departing from the spirit and scope of the invention.

What is claimed is:

1. A trap, for selective use as a component of a dental or surgical evacuation system, which system includes an aspirator and a flexible suction conduit as other components thereof; in which evacuation system said suction conduit includes means at one end defining a coupling orifice, said aspirator includes means at one end defining a coupling nipple, and said conduit coupling orifice and said aspirator coupling nipple are configured for coacting coupling and sealing engagement with each other; said trap comprising an elongated housing having means defining a cylindrical coupling nipple at one end, having an outer diameter of 7/16 inch; said housing having a through passage, including a small bore portion at said one end passing through said nipple, and including a cylindrical counter bore opening to the end of said housing opposite from said nipple;

a retainer having a cylindrical body dimensioned to be received in said housing counterbore with a sliding sealing fit, and having radially enlarged gripping means at one end for manipulating the retainer relative to said housing; said retainer having an axial through passage including means defining a coupling orifice at said one end; said retainer coupling orifice being defined by a bore having a 7/16 inch taper;

a filter element confined in said housing by said retainer; said filter element traversing said housing through passage and defining, with said housing and said retainer, a collection chamber;

said housing coupling nipple being configured for coacting frictional coupling and sealing engagement with said conduit coupling orifice, the coupling orifice of which is defined by a bore having a 7/16 inch taper and is a counterpart of said retainer coupling orifice; and said retainer coupling orifice being configured for coacting frictional coupling and sealing engagement with said aspirator coupling nipple, the coupling nipple of which has an outer diameter of 7/16 inch and is a counterpart of said housing coupling nipple.

2. A trap as set forth in claim 1
said retainer gripping means comprising a radial flange provided with a peripheral serrated surface.

3. A trap as set forth in claim 1
said housing and said retainer being fabricated from a plastic material.

4. A trap as set forth in claim 1
said housing and said retainer being fabricated from tetrafluoroethylene.

5. A trap as set forth in claim 1
said housing counterbore providing, with said smaller bore portion, a transverse annular shoulder; the inner end of said retainer defining an annular end face confronting said shoulder, with said body having a length to enable abutting engagement of said shoulder and end face; and said filter element being configured to seat on said shoulder, and to be retained thereon by said retainer end face; said filter element, said housing counterbore, and said retainer passage thereby defining said collection chamber of said trap.

6. A trap as set forth in claim 1
said filter element comprising a pliable bag formed with an open end from a filtering material; said bag being disposed within said housing counterbore, with its open end coinciding with the open end of said counterbore, and with its closed end maintained in spaced relation from said housing smaller bore portion; and said retainer body being received within the open end of said filter bag and said housing counterbore to retain said bag in said housing, said bag thereby defining said collection chamber of said trap.

7. A trap as set forth in claim 6
said bag being formed from a cloth fabric; the open end of said bag being frictionally retained between said housing counterbore and said retainer.

8. A trap as set forth in claim 1
said means defining a coupling orifice at one end of said suction conduit comprising an adaptor at said one end; said adapter having a bore defining said coupling orifice.

* * * * *